United States Patent
Pandey et al.

(10) Patent No.: US 6,765,015 B2
(45) Date of Patent: Jul. 20, 2004

(54) HALOGENATED PACLITAXEL DERIVATIVES

(75) Inventors: Ramesh C. Pandey, Highland Park, NJ (US); Luben K. Yankov, Edison, NJ (US)

(73) Assignee: Xechem International, Inc., New Brunswick, NJ (US)

( * ) Notice: Subject to any disclaimer, the term of this patent is extended or adjusted under 35 U.S.C. 154(b) by 237 days.

(21) Appl. No.: 09/938,041

(22) Filed: Aug. 23, 2001

(65) Prior Publication Data

US 2002/0107409 A1 Aug. 8, 2002

Related U.S. Application Data

(63) Continuation of application No. 08/974,404, filed on Nov. 19, 1997, now abandoned, which is a continuation-in-part of application No. 08/936,710, filed on Sep. 24, 1997, now abandoned, and a continuation-in-part of application No. 08/654,424, filed on May 29, 1996, now Pat. No. 5,807,888, and a continuation-in-part of application No. 08/672,397, filed on May 29, 1996, now Pat. No. 5,854,278, and a continuation-in-part of application No. 08/572,240, filed on Dec. 13, 1995, now Pat. No. 5,654,448.

(51) Int. Cl.$^7$ .................. A61K 31/337; C07D 305/14
(52) U.S. Cl. .................. 514/449; 549/510; 549/511
(58) Field of Search .................. 514/449; 549/510, 549/511

(56) References Cited

U.S. PATENT DOCUMENTS 5,608,102 A * 3/1997 Bourzat et al. .............. 560/39

* cited by examiner

*Primary Examiner*—Ba K. Trinh
(74) *Attorney, Agent, or Firm*—W. Dennis Drehkoff; Ladas & Parry

(57) ABSTRACT

This invention is directed to novel halogenated paclitaxel derivatives, processes for their preparation and use as effective anti-tumor agents.

35 Claims, No Drawings

HALOGENATED PACLITAXEL DERIVATIVES

This is a continuation of co-pending application Ser. No. 08/974,404 filed Nov. 19, 1997, now abandoned.

RELATED APPLICATIONS

This Application is a continuation-in-part of U.S. application Ser. No. 08/572,240, filed Dec. 13, 1995, now U.S. Pat. No. 5,654,448, U.S. application Ser. No. 08/654,424, filed May 29, 1996, and U.S. application Ser. No. 08/672,397, filed May 29, 1996, now U.S. Pat. Nos. 5,807,888 and 5,824,278, respectively, and U.S. Ser. No. 08/936,710, filed Sep. 24, 1997, now pending.

FIELD OF THE INVENTION

This invention is directed to novel halogenated paclitaxel analogs and derivatives, processes for their preparation and use as effective anti-tumor agents.

BACKGROUND OF THE INVENTION

Several important compounds from the taxane family of terpenes have been identified as possessing strong antineoplastic activity against various cancers. For example, paclitaxel (1), having the following structure,

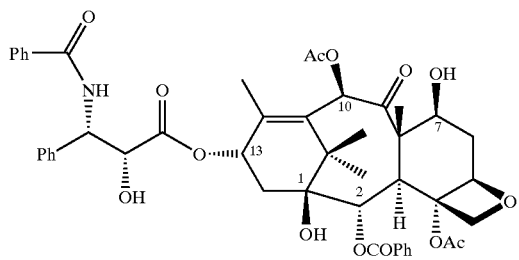

has been approved by the Food and Drug Administration for the treatment of ovarian cancer and breast cancer, and is presently undergoing clinical trials for treatment of various other cancers, including lung and colon cancer.

Cephalomannine has been reported to be effective in causing remission of leukemic tumors (see U.S. Pat. No. 4,206,221) and is most often present with its structurally similar analog, paclitaxel. The structure of cephalomannine (2) is shown below:

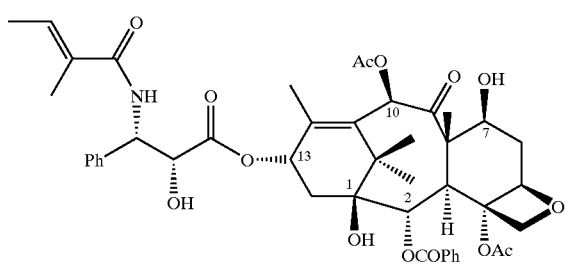

Paclitaxel and cephalomannine are only some of the many natural products from the taxane family which can be found, for example, in the bark of the Pacific yew tree *Taxus brevifolia* and other yew species such as *T. baccata, T. cuspidata*, as well as *T. yunnanensis* and other plant materials including *T. hicksii, T. densiformis, T. gem. T wardii, T. capitata, T. brownii*, and T. dark green spreader. These compounds can also be found in Cephalotaxus species, such as, for example, *Cephalotaxus manni* as well as cultured plant cells and fungi.

The supply of paclitaxel, cephalomannine and other important taxanes is, however, limited to a finite amount of yew trees and other vegetation in which they are present in small amounts. Thus, alternative compounds having paclitaxel-like or cephalomannine-like anti-tumor activity are highly desirable to increase the armamentarium of clinical therapeutic agents.

In the U.S. application Ser. No. 08/654,424, filed May 29, 1996, and U.S. application Ser. No. 08/672,397, filed May 29, 1996, now U.S. Pat. Nos. 5,807,888 and 5,824,278 respectively, the entirety of each being incorporated by reference herein, the synthesis, separation and anticancer activity of several dihalocephalomannine diastereomers is provided. In this study, two diastereomeric 2", 3"-dibromocephalomannines and their two corresponding 7-epimers were obtained by treatment of extracts of *Taxus yunnanensis* with bromine solution, under mild conditions. Treatment of the same extract with chlorine solution yielded four diastereomeric 2", 3"-chlorocephalomannines. The diastereomeric mixtures were separated into the individual components by preparative HPLC on $C_{18}$ reversed-phase silica gel. A more efficient analytical separation seas obtained on a penta-fluorophenyl bonded phase. The compounds were isolated and fully identified by classic and modem methods. Slight differences were observed in the NMR spectra of the 7-epimers when compared to their 7β-OH analogs. On the basis of a comparison of physicochemical data, the bromo compounds were identified as (2"R,3"S)-dibromo-7-epi-cephalomannine (3), (2"S,3"R)-dibromo-7-epi-cephalomannine (4), (2"R,3"S)-dibromo-cephalomannine (5), (2"S,3"R)-dibromocephalomannine (6). The chloro compounds were identifed as (2"R,3"R)-dichlorocephalomannine (7), (2"S,3"S)-dichlorocephalomannine (8), (2"R,3"S)-dichlorocephalomannine (9), and , (2"S,3"R)-dichlorocephalomannine (10).

Cytotoxic activity was tested against the NCI 60 human tumor cell line panel in comparison with paclitaxel and results were obtained showing strong antineoplastic activity against several tumor lines, including, but not limited to, leukemia cell line HL-60 (TB); Non-Small Cell Lung Cancer Line NCI-H522; Colon Cancer Cell Lines COO 205 and HT29, CNS Cancer Cell Lines SF-539 and SNB-75; Ovarian Cancer Cell Line OVCAR-3; Renal Cancer Cell Line RXF-393; and Breast Cancer Cell Lines MCF7, MDA-MB-231/ATCC, HS 578, MDA-MB-435 and MDA-N.

The structures of some of these dihalogenated cephalomannines are set forth below:

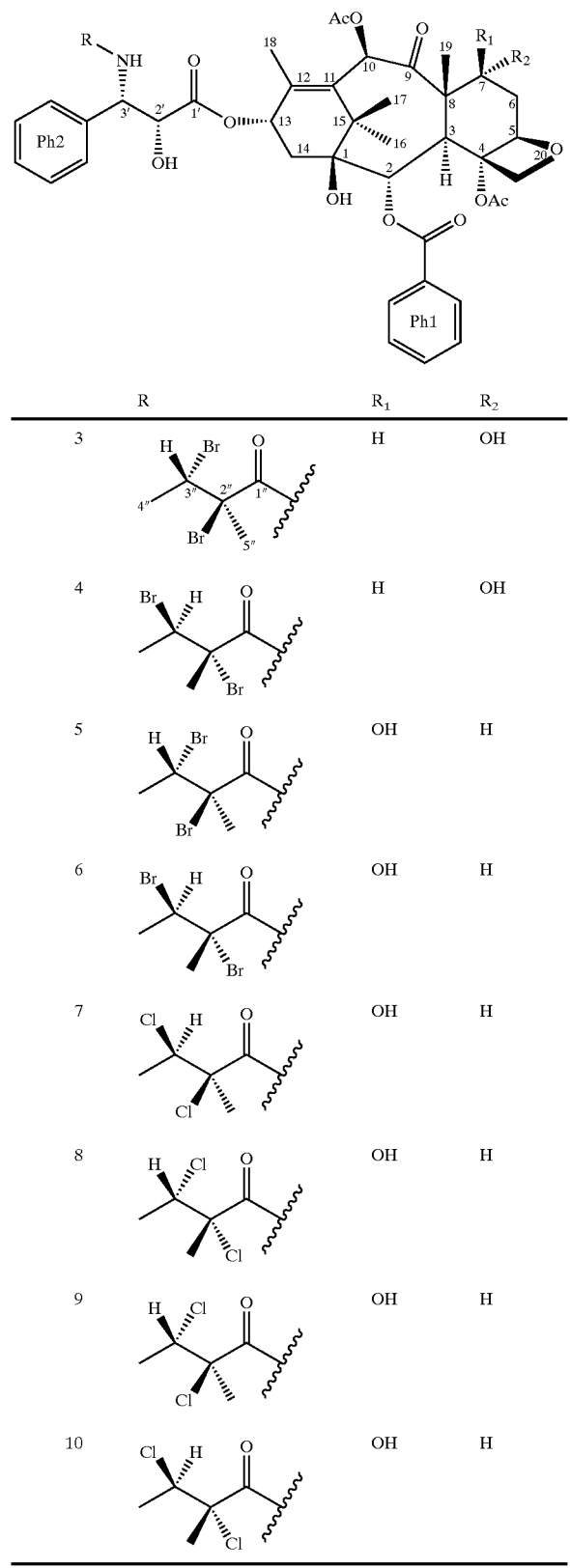

SUMMARY OF THE INVENTION

In accordance with the present invention, there are now provided several novel halogenated derivatives of paclitaxel and cephalomannine for use as anticancer agents, which have structures selected from the next two general formulas A and B:

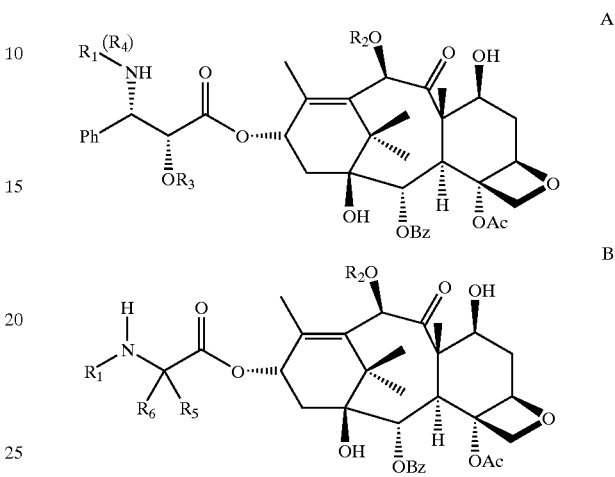

For General Formula A:
wherein $R_1$ is mono or dihalogenated acyl group, aroyl group (Table 1), alkyloxy-carbonyl group or aryloxy-carbonyl group (Table 2) and $R_3$ is hydrogen or halogenated group, and $R_2$ is hydrogen or acetyl groups;
wherein $R_4$ is PhCO or $Me_3COCO$ or $CH_3CH=C(CH_3)CO$, $R_3$ is a halogenated group (Tables 1 and 2);

For general formula B:
wherein $R_1$ is mono or dihalogenated acyl group or aroyl group (Table 1), alkyloxy-carbonyl group or aryloxy-carbonyl group (Table 2) and $R_2$ is hydrogen or acetyl group, and $R_5$ is any group from Table 3;
$R_6$ is H or Me;

TYPE I

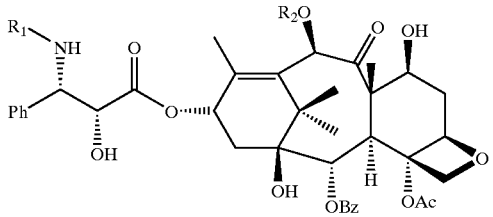

wherein
$R_1$ is a group selected from Table 1 (groups 1 to 40); and $R_2$ is H or Ac;

TABLE 1

Structures of Halogenated Acyl and Aroyl Groups

Group 1

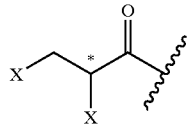

TABLE 1-continued
Structures of Halogenated Acyl and Aroyl Groups
Group 2 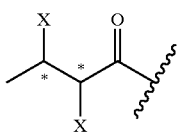
Group 3 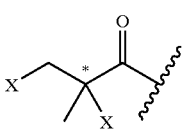
Group 4 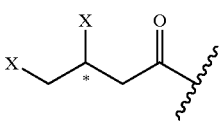
Group 5 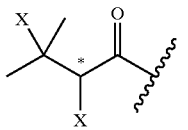
Group 6 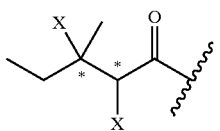
Group 7 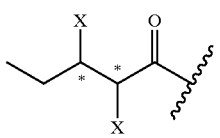
Group 8 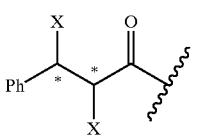
Group 9 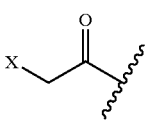
Group 10 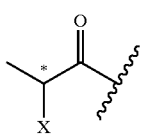
Group 11 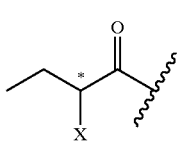
Group 12 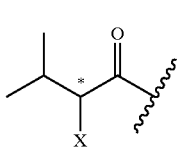
TABLE 1-continued
Structures of Halogenated Acyl and Aroyl Groups
Group 13 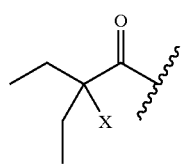
Group 14 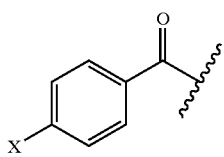
Group 15 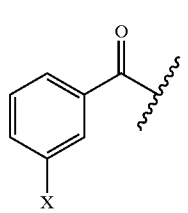
Group 16 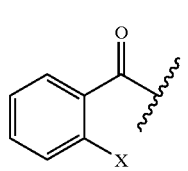
Group 17 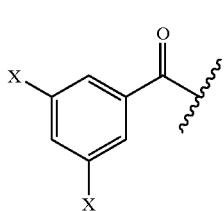
Group 18 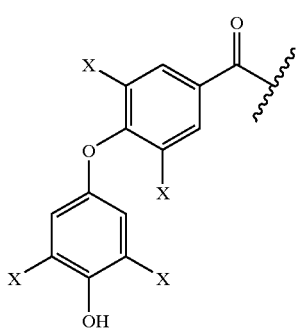
Group 19 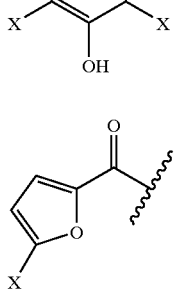

TABLE 1-continued

Structures of Halogenated Acyl and Aroyl Groups

| Group | Structure |
|---|---|
| Group 20 | 5-halothiophene-2-carbonyl |
| Group 21 | 5-halo-1H-pyrrole-2-carbonyl |
| Group 22 | 5-halopentanoyl |
| Group 23 | 2-halohexanoyl |
| Group 24 | 3-halo-2,2-dimethylpropanoyl |
| Group 25 | 6-halohexanoyl |
| Group 26 | 4-halobutanoyl |
| Group 27 | 4-halo-3,3-dimethylbutanoyl |
| Group 28 | 2,3-dihalo-3-phenylpropanoyl |
| Group 29 | 2,4-dihalobenzoyl |
| Group 30 | 2,6-dihalobenzoyl |
| Group 31 | 3,4-dihalobenzoyl |
| Group 32 | 5-halopyridine-2-carbonyl |
| Group 33 | 5-halopyridine-3-carbonyl |
| Group 34 | 3-haloquinoline-2-carbonyl |
| Group 35 | 3,5-dihalobenzoyl |
| Group 36 | trihalobenzoyl ($X_1$, $X_2$, $X_2$) |
| Group 37 | 4-(halomethyl)benzoyl |

TABLE 1-continued

Structures of Halogenated Acyl and Aroyl Groups

Group 38
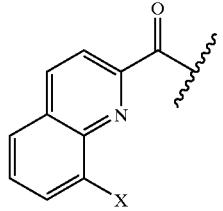

Group 39
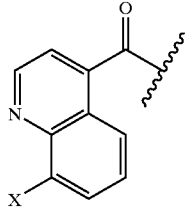

Group 40
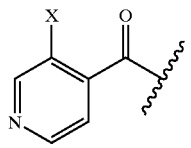

X: halogen (Cl or Br or I or F)
X$_1$: one type of halogen
X$_2$: other type of halogen

TABLE 2

Structures of Halogenated Alkyloxy- and Aryloxy- Carbonyl Groups

Group 41
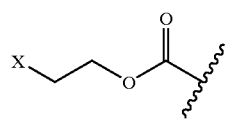

Group 42
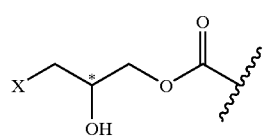

Group 43
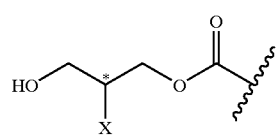

Group 44
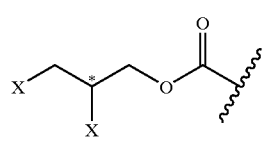

Group 45
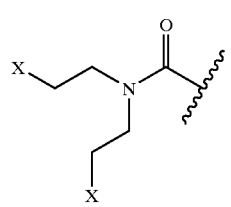

TABLE 2-continued

Structures of Halogenated Alkyloxy- and Aryloxy- Carbonyl Groups

Group 46
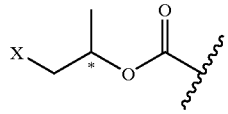

Group 47
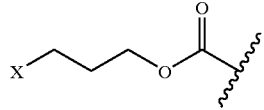

Group 48
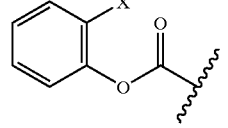

Group 49
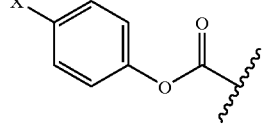

Group 50
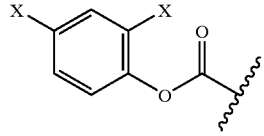

Group 51
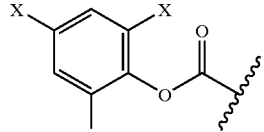

Group 52
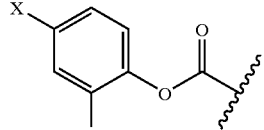

Group 53
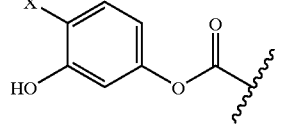

Group 54
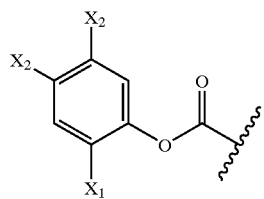

TABLE 2-continued
Structures of Halogenated Alkyloxy- and Aryloxy- Carbonyl Groups
Group 55
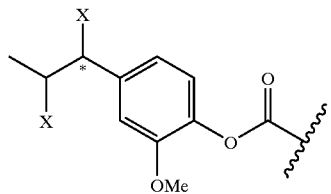
Group 56
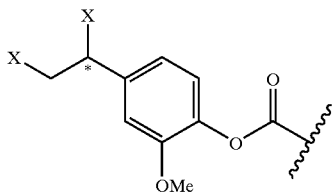
Group 57
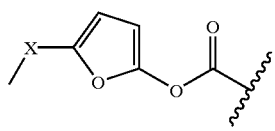
Group 58
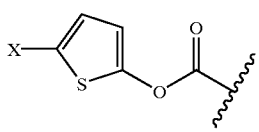
Group 59
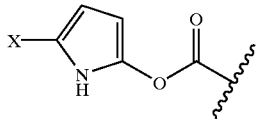
Group 60
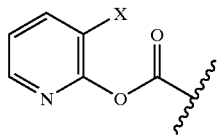
Group 61
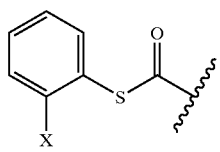
Group 62
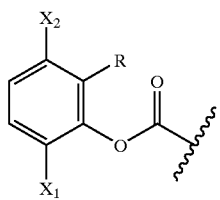
Group 63
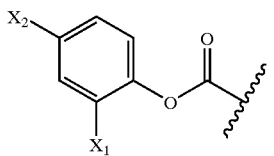
TABLE 2-continued
Structures of Halogenated Alkyloxy- and Aryloxy- Carbonyl Groups
Group 64
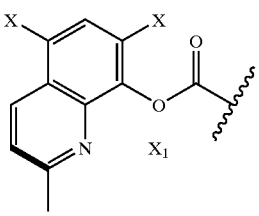
Group 65
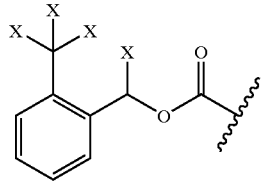
Group 66
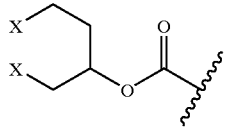
Group 67
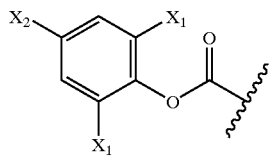
Group 68
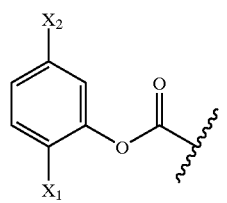
Group 69
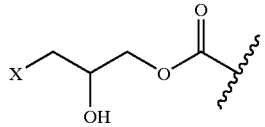
Group 70
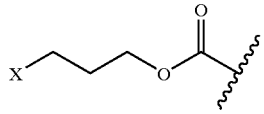
Group 71
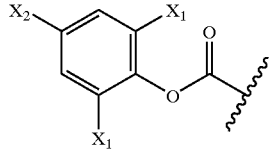

TABLE 2-continued
Structures of Halogenated Alkyloxy- and Aryloxy- Carbonyl Groups
Group 72
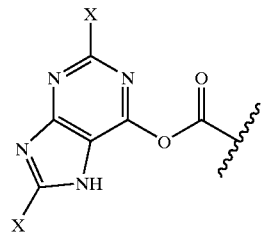
Group 73
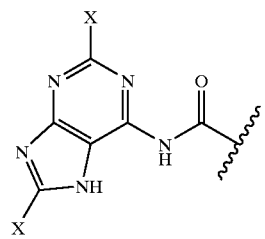
Group 74
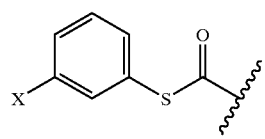
Group 75
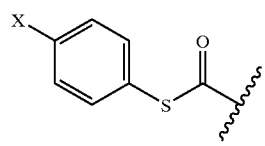
Group 76
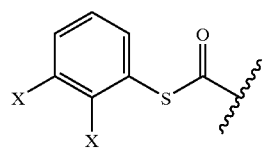
Group 77
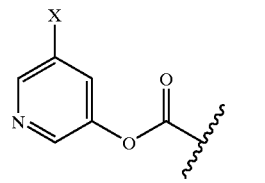
Group 78
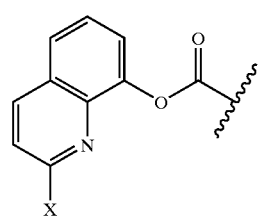
Group 79
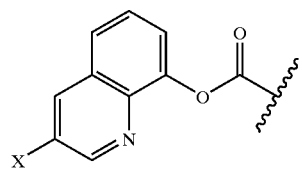
TABLE 2-continued
Structures of Halogenated Alkyloxy- and Aryloxy- Carbonyl Groups
Group 80
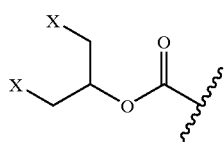
Group 81
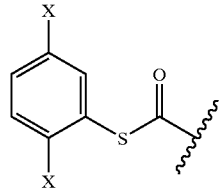
Group 82
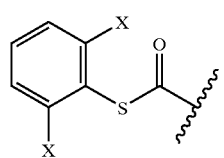
Group 83
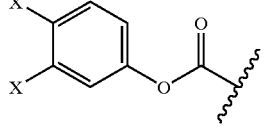
Group 84
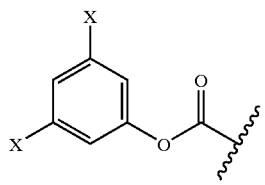
Group 85
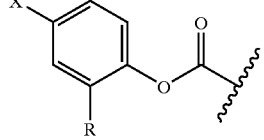
Group 86
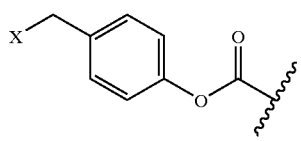
Group 87
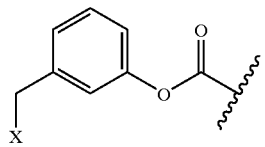
Group 88
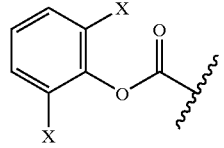

TABLE 2-continued

Structures of Halogenated Alkyloxy- and Aryloxy- Carbonyl Groups

Group 89
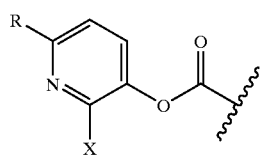

Group 90
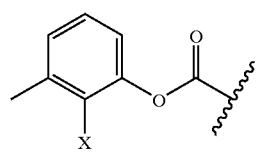

Group 91
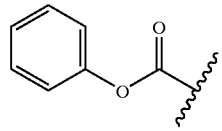

Group 92
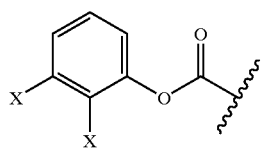

Group 93
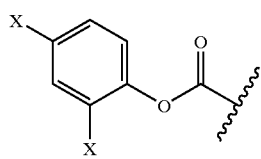

Group 94
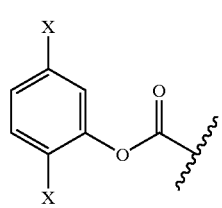

Group 95
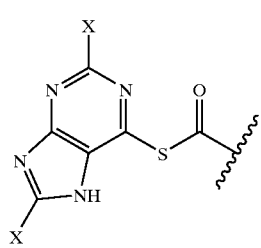

X: halogen (Cl or Br or I or F)
$X_1$: one type of halogen
$X_2$: other type of halogen

TABLE 3

Group Structures of Amino Acids and Their Codes Used in This Patent

Me

TABLE 3-continued

Group Structures of Amino Acids and Their Codes Used in This Patent

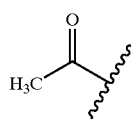

Ac

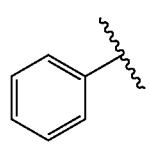

Ph

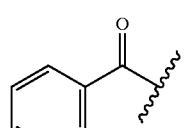

Bz

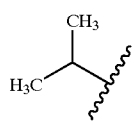

$G_1$

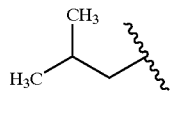

$G_2$

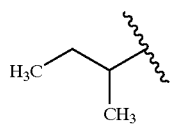

$G_3$

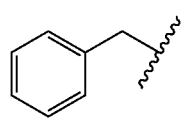

$G_4$

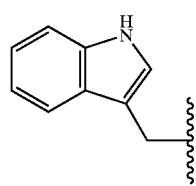

$G_5$

TABLE 3-continued

Group Structures of Amino Acids and Their Codes Used in This Patent

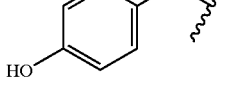
G$_6$

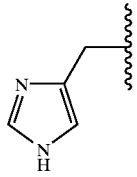
G$_7$

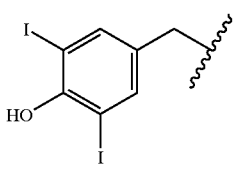
G$_8$

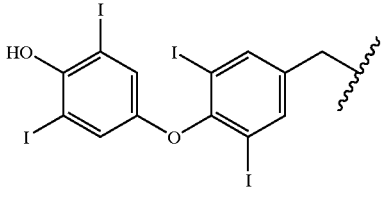
G$_9$

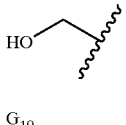
G$_{10}$

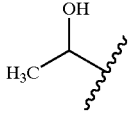
G$_{11}$

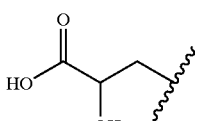
G$_{12}$

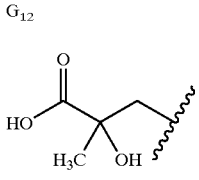
G$_{13}$

TYPE II

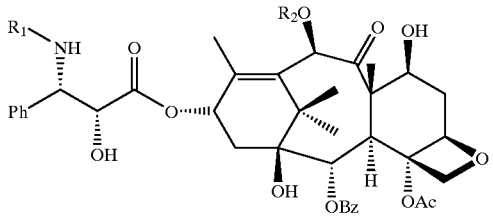

wherein
R$_1$ is a group selected from Table 2 (groups 41 to 95);
R$_2$ is H or Ac;

TYPE III

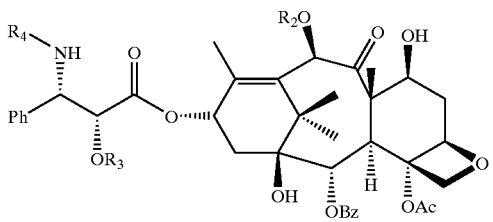

wherein
R$_3$ is a group selected from Table 1 (groups 1 to 40);
and R$_2$ is H or Ac, and R$_4$ is PhCO or Me$_3$COCO or CH$_3$CH=C(CH$_3$)CO;

TYPE IV

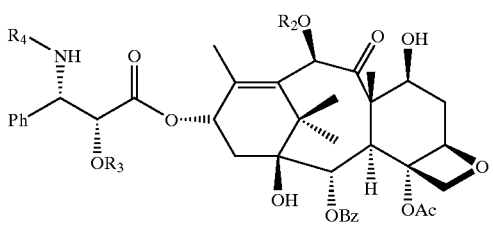

wherein
R$_3$ is a group selected from Table 2, (groups 41 to 95),
R$_2$ is Ac or H, and R$_4$ is PhCO or Me$_3$COCO or CH$_3$CH=C(CH$_3$)CO;

TYPE V

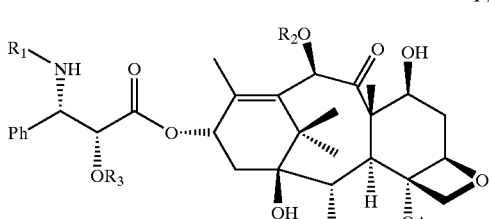

wherein
R$_1$ is a group selected from Table 1 (groups 1 to 40);
R$_2$ is H or Ac;
R$_3$ is a group selected from Table 2 (groups 41 to 95);

TYPE VI

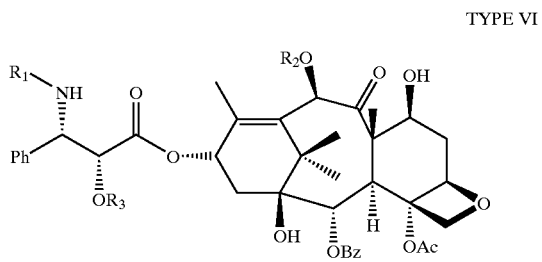

wherein
R₁ is a group selected from Table 2 (groups 41 to 95);
R₂ is H or Ac;
R₃ is a group selected from Table 1 (groups 1 to 40);

TYPE VII

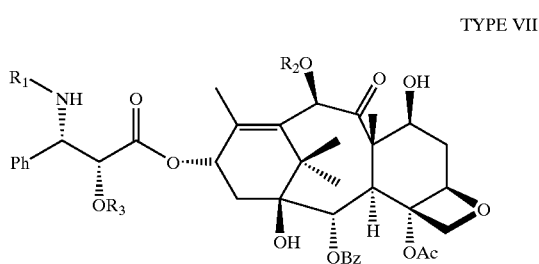

wherein
R₁ is a group selected from Table 1 (groups 1 to 40);
R₂ is H or Ac;
R₃ is a group selected from Table 1 (groups 1 to 40);

TYPE VIII

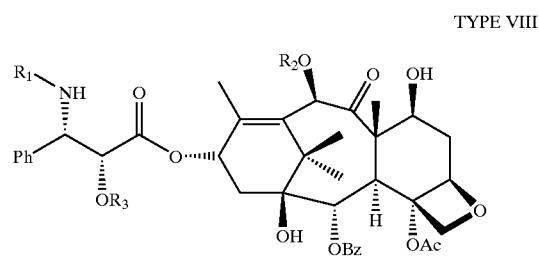

wherein
R₁ is a group from Table 2 (groups 41 to 95);
R₂ is H or Ac;
R₃ is a group selected from Table 2 (groups 41 to 95);

TYPE IX

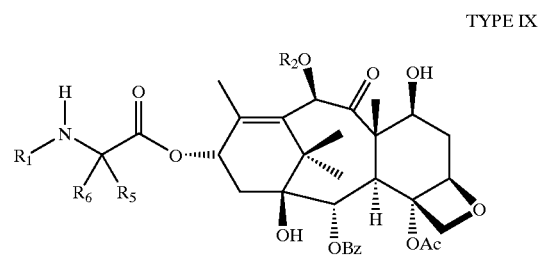

wherein
R₁ is a group selected from Table 1 (groups 1 to 40);
R₂ is H or Ac;
R₅ is H or Me or Ac or Ph or Bz or G₁ or G₂ or G₃ or G₄ or G₅ or G₆ or G₇ or G₈ or G₉ G₁₀ or G₁₁ or G₁₂ or G₁₃;
R₆ is H, only in the case when R₅ is G₁₀ the group R₆ is H or Me;

TYPE X

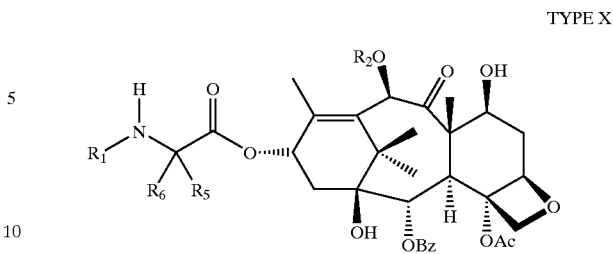

wherein
R₁ is a group selected from Table 2 (groups 55 to 95);
R₂ is H or Ac;
R₅ is H or Me or Ac or Ph or Bz or G₁ or G₂ or G₃ or G₄ or G₅ or G₆ or G₇ or G₈ or G₉ G₁₀ or G₁₁ or G₁₂ or G₁₃;
R₆ is H, only in the case when R₅ is G₁₀ the group R₆ is H or Me;

DETAILED DESCRIPTION OF THE INVENTION WITH PREFERED EMBODIMENTS

Synthesis of the Compounds
General Method

In accordance with this invention, halogenated cephalomannine, paclitaxel or other taxane analogs can be prepared in good yields from relatively refined sources of cephalomannine, paclitaxel and other taxane compounds. The analogs are prepared by selective halogenation of the different aliphatic or aromatic saturated or unsaturated acids, further converted to acyl halogenides or halogenated aliphatic or aromatic unsaturated alchohols or phenols, converted with phosgene to the corresponding formates, while leaving portions or moieties of the molecule or other important taxane compounds in the mixture, such as 10-deacetyl-baccatin III, Baccatine III, Cephalomannine, Taxotere, Paclitaxel, undisturbed and unreacted.

Separation and purification of halogenated analogs which show strong antitumor efficacy from the mixture can be accomplished by conventional or other modem methods.

Halogenation of unsaturated or saturated aliphatic or aromatic acids can be done by some classical reactions bubolling the halogene through the cold solution of the above mention compounds or by addition dropwise or pure halogene or disolved in nonpolar solvents as methylene chloride, ethylene dichloride, chloroform, carbon tetrachloride, following by separation and purification of the resulting less polar mixture to individual pure compounds using classical or modem methods (destilation, crystalization, chromatography etc.).

Halogenation of unsaturated or saturated alcohols or phenols can be done using the methods so close to these used for production of halogenated aliphatic or aromatic acids.

The synthetic methods of this invention are advantageously independent of the concentration of starting compunds with taxan structure present in various bulk products as 10-deacetyl-baccatin III, Baccatin III, debenzoyleted cephalomannine and Paclitaxel or Cephalomannine Taxotere and Paclitaxel.

All of them can be obtained from natural sources, or by synthetic or semisynthetic methods.

The reaction between mono-or dichalogenated acyl halogenides, can be done in solution of nonpolar solvents as dichloromethane, dichloroethane, chloroform, carbontetrachloride at room (or lower) temperature in presents of some organic or inorganic reagents as N,N,N,-triethylamine, pyridine etc., to catch the HX coming from the reaction.

On the same way are provided and the reactions between halogenated alcyl (or aryl-)-oxy-carbonyl-halogenides with amino acids or taxane derivatives.

There are different ways for preparation of formates: 1. Preparation of formates from halogenated alchohols or phenols by reaction with phosgene, followed by purification or the product. Next step is the reaction of the formate with amino acids or taxane derivatives.

In the last reaction can be used ready made formates. 2. Combined (one step) reaction between halogenated derivatives (alcohols or phenols), phosgene and amino acids or taxane compounds.

All reactions of this invention are shown on the following schematic diagram (Reactions I to VII).

Reaction I

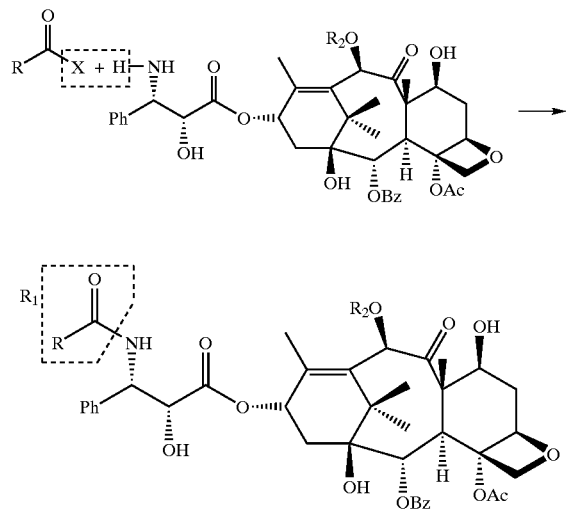

$R_1$ = Halogenated acyl Groups (see Table 1)
$R_2$ = Ac or H

Reaction II, Variant A

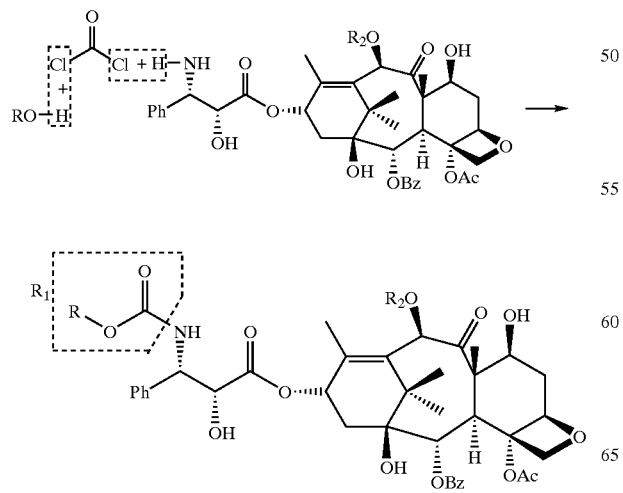

Reaction II, Variant B

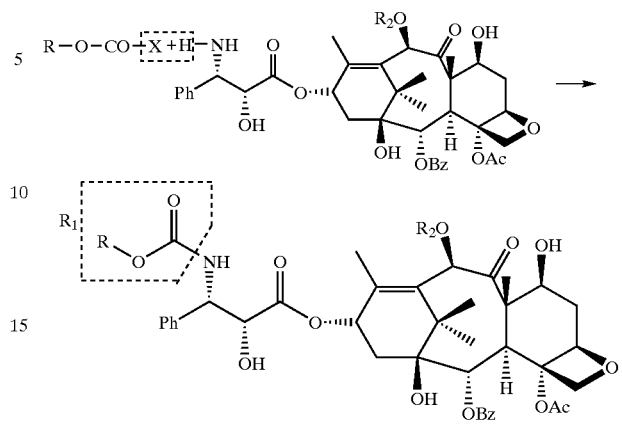

$R_1$ = Halogenated Alkyloxy-or Aryloxy-Carbonyl Groups
$R_2$ = Ac or H

Reaction III

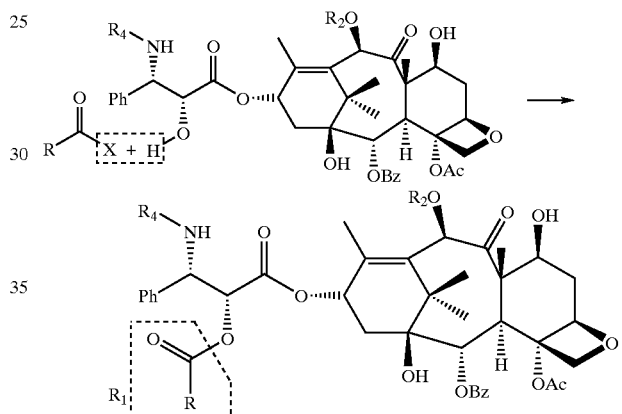

$R_1$ = Halogenated acyl Groups (see Table 1)
$R_2$ = Ac or H
$R_4$ = PhCO or Me$_3$COCO or CH$_3$CH = C(CH$_3$)CO Reaction IV Variant A

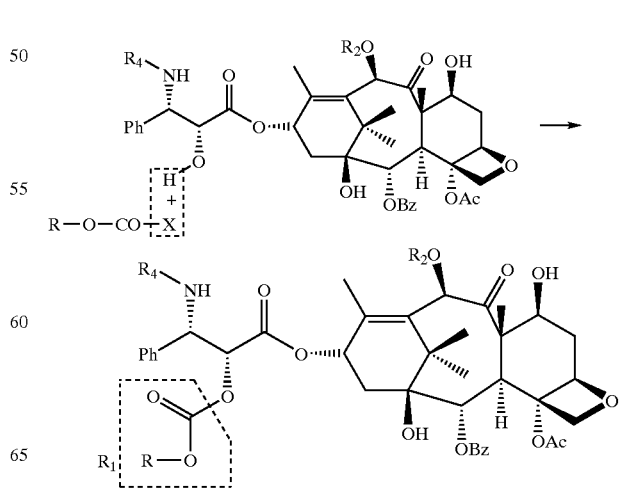

-continued

Variant B

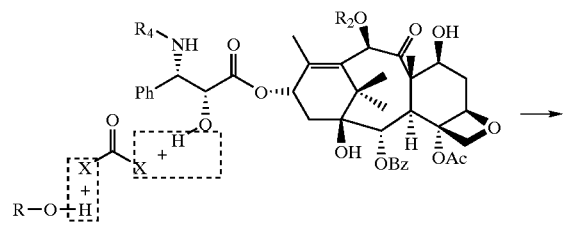

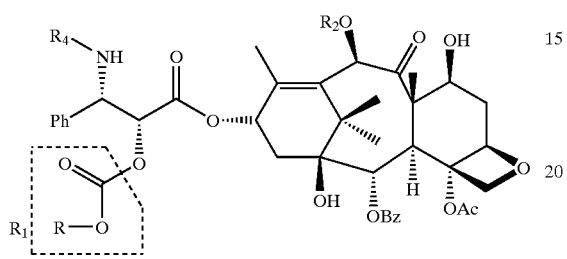

$R_1$ = Halogenated Alkyloxy-or Aryloxy-Carbonyl Groups
$R_2$ = Ac or H    (see Table 2)
$R_4$ = PhCO pr Me$_3$COCO or CH$_3$CH = (CH$_3$)CO

Reaction V

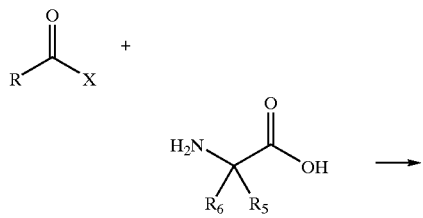

$R_1$ = Halogenated acyl Groups    (see Table 1)
$R_5$ = H or Me or Ac or Ph or Bz or $G_1$ or $G_2$ or $G_3$ or $G_4$ or $G_5$ or $G_6$ or $G_7$ or $G_8$ or $G_9$ or $G_{10}$ or $G_{11}$ or $G_{12}$ or $G_{13}$    (see Table 3)
$R_6$ = H or Me

Reaction VI

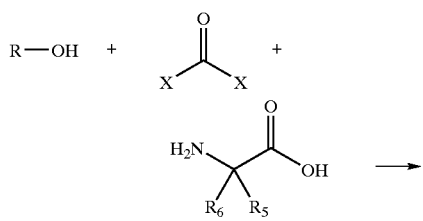

-continued

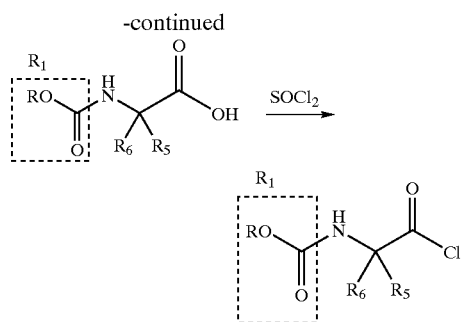

$R_1$ = Halogenated alkyloxy-or aryloxy-carbonyl Groups    (see Table 2)
$R_2$ = Ac or H
$R_5$ = H or Me or Ac or Ph or Bz or $G_1$ or $G_2$ or $G_3$ or $G_4$ or $G_5$ or $G_6$ or $G_7$ or $G_8$ or $G_9$ or $G_{10}$ or $G_{11}$ or $G_{12}$ or $G_{13}$    (see Table 3)
$R_6$ = H or Me

Reaction VII

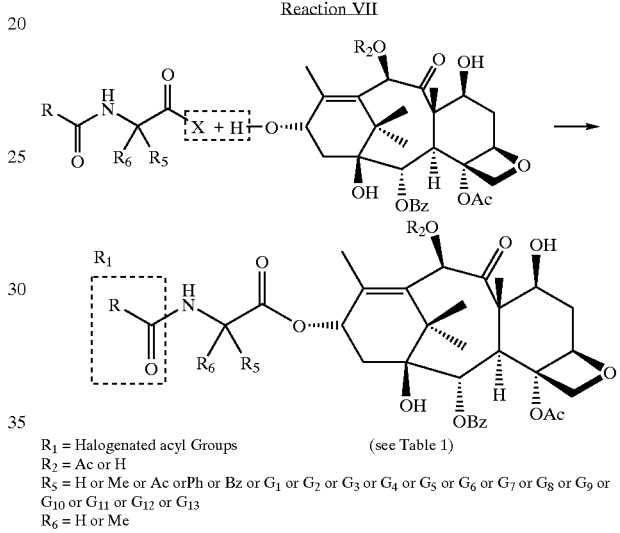

$R_1$ = Halogenated acyl Groups    (see Table 1)
$R_2$ = Ac or H
$R_5$ = H or Me or Ac orPh or Bz or $G_1$ or $G_2$ or $G_3$ or $G_4$ or $G_5$ or $G_6$ or $G_7$ or $G_8$ or $G_9$ or $G_{10}$ or $G_{11}$ or $G_{12}$ or $G_{13}$
$R_6$ = H or Me

Reaction VIII

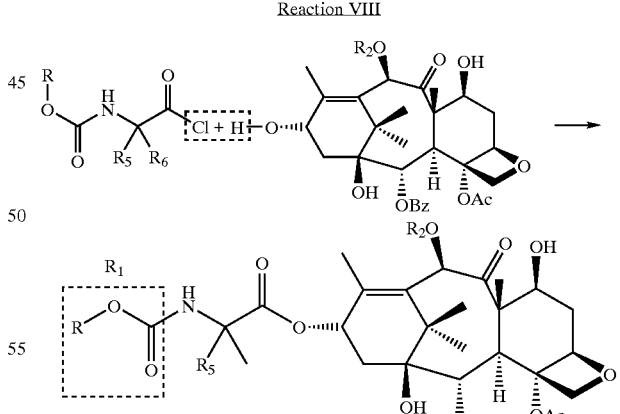

$R_1$ = Halogenated alkyloxy-or aryloxy-carbonyl Groups    (see Table 2)
$R_2$ = Ac or H
$R_5$ = H or Me or Ac or Ph or Bz or $G_1$ or $G_2$ or $G_3$ or $G_4$ or $G_5$ or $G_6$ or $G_7$ or $G_8$ or $G_9$ or $G_{10}$ or $G_{11}$ or $G_{12}$ or $G_{13}$
$R_6$ = H or Me The resulting pure halogenated compounds can be separated and their chemical structures elucidated by conventional, analytical and physicochemical techniques.

The reaction mixture containing taxane impurities can then be separated and purified by conventional methods such as chromatography and recrystallization and the individual separated and halogenated analogs made available for antitumor treatment.

Synthesis of Compounds of Type I

Halogenated paclitaxel analogs of the general structure Type I of this invention can be prepared by the following synthetic route:

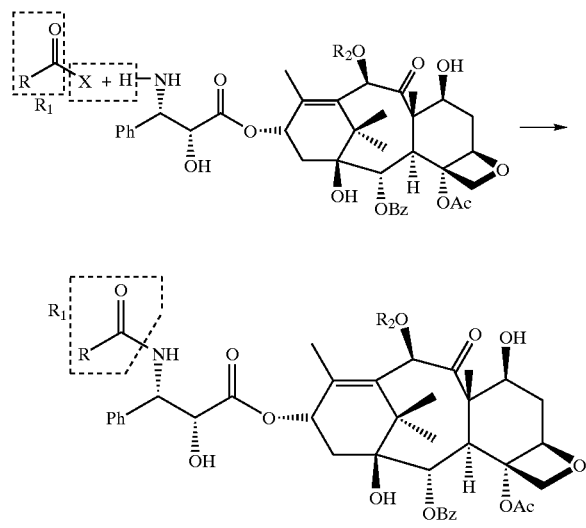

where $R_1$ is a dihalogenated or halogenated acyl group selected from Table 1, groups 1–40, and $R_2$ is H or Ac.

EXAMPLE 1

The reaction scheme in the production of Type I compounds is further exemplified by N-(2"-bromo-3"methyl)-butanoyl-N-debenzoyl-cephalomannine which can be prepared as follows:

7.49 g (0.010 M) N-debenzoyl-cephalomannine is dissolved in 200 ml anhydrous 1,2-dichloro-ethane (DE) and to this solution at room temperature is added 3.05 g (0.030 M) N,N,N-triethylamine (TEA), dissolved in 25 ml dry 1,2-dichloro-ethane (DE).

The mixture is stirred and cooled in an ice bath to 0° C. 10 for about 1 hour.

During stirring at 0° C., 4.99 g (0.025 M)2-bromo-3-methyl-butanoyl-chloride dissolved in 25 ml dry DE is added dropwise and the mixture stirred at 0° C. for approximately 5 hours.

After the reaction is finished, the mixture is washed 3 times (each time with 200 ml) with water and the organic layer is dried over on 10 g anhydrous $Na_2SO_4$ overnight.

The dry solution is filtered and concentrated to a dry solid material on a Buchi Rotovapor at 40° C. and high vacuum to produce 8.0–9.5 g solid creamy material.

This material is purified on a preparative HPLC reversed phase C-18 column and mobile phase 45/55 acetonitrile/water.

After sedimentation and crystallization from 50/50 acetone/hexane, 6.8 g of a white crystalline solid is obtained (yield of 75%).

Synthesis of Compounds Type II

Halogenated analogs of paclitaxel of the general structure of Type II in accordance with this invention can be prepared by the following synthetic route:

VARIANT A

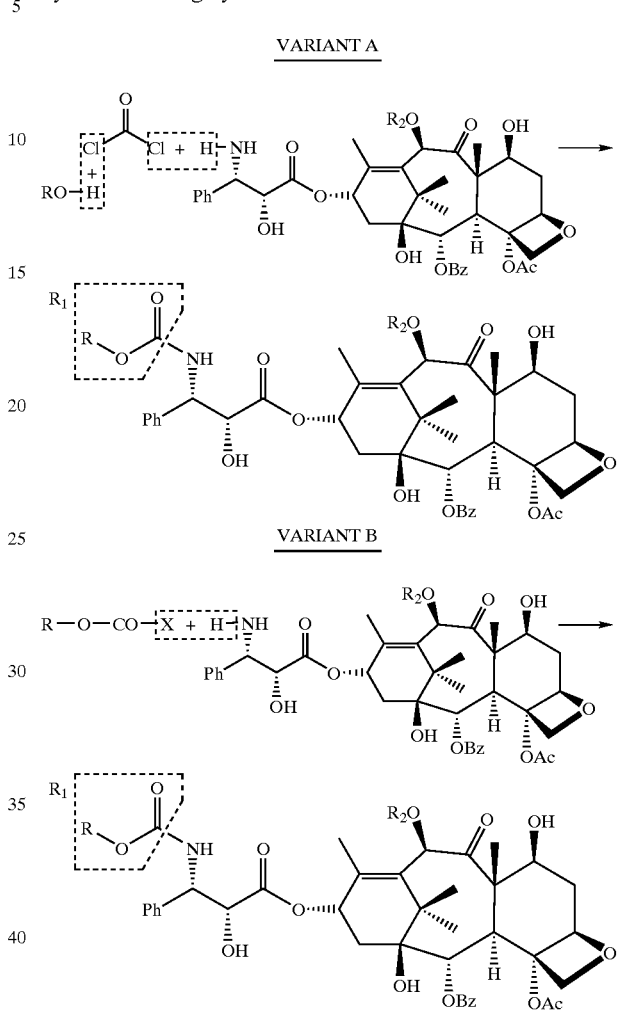

VARIANT B where $R_1$ is a halogenated group selected from Table 2, groups 41–95, R is a halogenated alchohol or phenol, and $R_2$ is Ac or H;

EXAMPLE 2

Variant A

The reaction scheme of Type II compounds is exemplified by N-(2,4-dibromophenoxy)carbonyl-N-detygloyl-cephalomannine which can be prepared as follows:

7.56 g (0.030 MO 2,4-dibromophenol is dissolved in 250 ml DE (anhydrous) and the solution is cooled in an ice bath at 0° C.

Under $N_2$ atmosphere at 0° C. and stirring, this solution is treated with 3.05 g (0.030 M), and 3.33 g solid triphosgene (0.012 M), and stirring at 0° is continued for one hour.

7.28 g (0.030 M) N-detygloyl-cephalomannine is dissolved in 120 ml anhydrous DE and the solution is stirred and cooled in an ice bath to 0° C.

Keeping the temperature around 0° C., the solution of 2,4-dibromophenylchloroformate is added dropwise to the cold (0° C.) solution of N-detygoyl-cephalomannine continuing the stirring 3 hours more.

The cooling bath is then removed and stirring is continued under $N_2$ atmosphere (at room temperature) for another 40 hours.

A new portion of 2,4-dibromophenyl-chloroformate (0.012 M), prepared by the same method above is added and stirring at room temperature continued for 3 days.

The reaction mixture (625–650 ml) is washed 3 times (each time with 500 ml) with water and the organic layer is dried over 40 g anhydrous $Na_2SO_4$ overnight.

After filtration, the solution is concentrated by drying on a Buchi Rotovapor at 40° C. and high vacuum.

The obtained crude material (about 12.5 g) is purified by preparative HPLC on a C-18 prep. Column using mobile phase 45/55 acetonitrile water.

The combined fractions which contain N-(2,4-dibromophenoxy)carbonyl-N-detygloyl cephalomannine are concentrated to remove acetonitrile and accumulated solid material recrystallized from 50/50 acetone/hexane.

7.12 g of white to off-white solid (yield 70–72%) is obtained.

EXAMPLE 3

Variant B

The reaction scheme of Type II compounds is further exemplified by N-(2,4-dibromoethoxy)carbonyl-N-detygloyl-cephalomannine which can be prepared as follows:

7.28 g (0.010 M) N-detygloyl-cephalomannine is dissolved in 200 ml anhydrous DE and to this solution at room temperature is added dropwise 3.05 g TEA (0.030 M). The mixture is stirred and cooled to 0° C. in an ice bath.

To this cold solution is added dropwise for few minutes 5.63 g (0.030 M) 2-bromoethylchloro-formate and reaction mixture continued to be stirred for 3 hours at 0° C.

When the reaction is finished, the mixture is washed 3 times (each time with 150 ml) with water and the washed organic layer dried with 10 g anhydrous $Na_2SO_4$ overnight.

The dry organic solution is filtered from desiccant and the clear solution concentrated to dryness on a Buchi Rotovapor at 40° C. and high vacuum.

The obtained 8.6–9.0 g dry material (residue) is purified by preparative HPLC on a C-18 reversed phase column using mobile phase 45/55 acetonitrile water.

The combined fractions which contain N-(2,4-dibromoethoxy)carbonyl-N-detygloyl-cephalomannine are concentrated and sedimented product is recrystallized from 50/50 acetone/hexane. 5.9 g of white crystalline product (yield 65%) are obtained.

SYNTHESIS OF COMPOUND OF TYPE III

Halogenated analogs of paclitaxel of the general structure of Type III can be prepared by the following synthetic route:

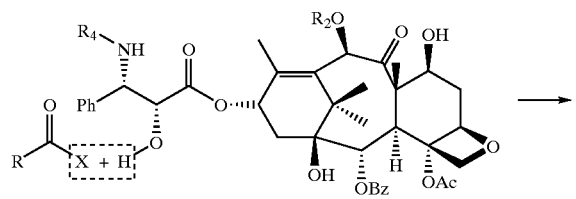

-continued

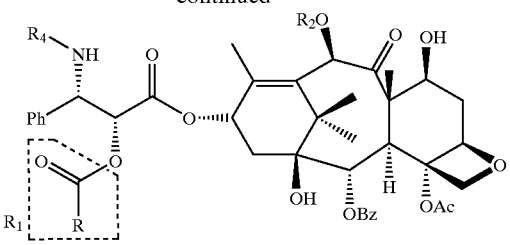

wherein $R_1$ is a halogenated or dihalogenated acyl group selected From Table 1, groups 1–40, $R_2$ is Ac or H, and $R_4$ is PhCO or $Me_3COCO$ or $CH_3CH=C(CH_3)CO$;

EXAMPLE 4

The reaction scheme of Type III compounds is exemplified by 2'-O-[(2,3-dichloro-3-phenyl)-propanoyl]-paclitaxel which can be prepared as follows:

8.53 g (0.010 M) paclitaxel is dissolved in 200 ml DE.

The mixture is stirred and cooled in an ice bathe to 0° C. for about 1 hour.

During the stirring at 0° C., to this solution is added dropwise 5.94 g (0.025 M) 2, 3-dichloro-3 phenyl-propanoyl chloride dissolved in 25 ml DE, and the stirring continued 5 hours at the same temperature.

After the finish of reaction, the mixture is washed 3 times (each time with 200 ml) with water and the washed organic extract dried on 10 g anhydrous $Na_2SO_4$ overnight.

The dry solution is filtered and concentrated to dryness on a Buchi Rotovapor at 40° C. and high vacuum to obtain 9.0–11.0 g dry white solid material.

The obtained crude product is purified on a preparative HPLC column C-18 using mobile phase 45/55 acetonitrile/water.

All fractions containing 2'-0-[(2,3-dichloro-3-phenyl)-propanoyl]-paclitaxel are combined and concentrated under vacuum, and the sedimented material filtered.

After crystallization from 50/50 acetone/hexane 8.20 g of white crystals (yield 72%) are obtained.

Synthesis of Compound of Type IV

Halogenated analogs of paclitaxel of the general structure of Type IV of this invention can be prepared by the following synthetic route:

Variant A

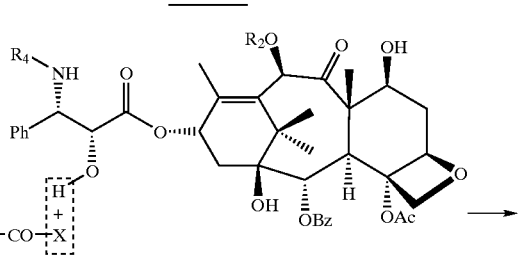

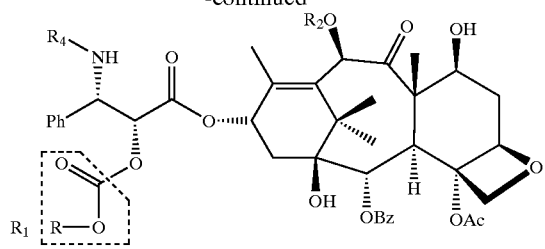

Variant B

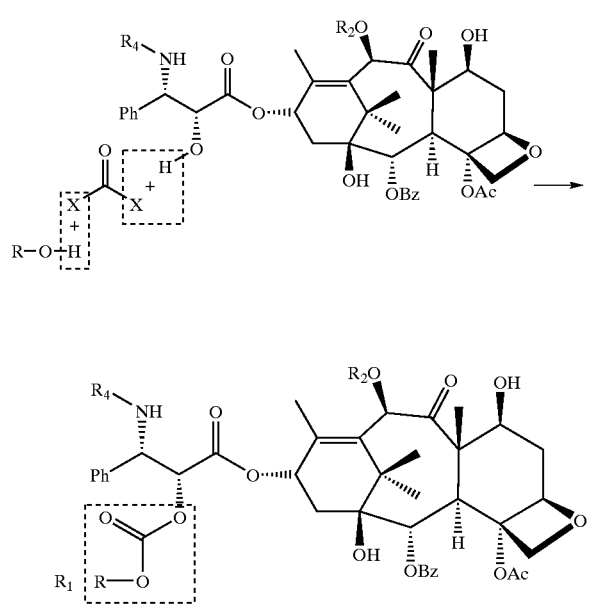

where $R_1$ is a halogenated or dihalogenated formate group (see Table 2, groups 41–95), $R_2$ is Ac or H, and $R_4$ is PhCO or $Me_3COCO$ or $CH_3CH=C(CH_3)CO$;

EXAMPLE 5

Variant A

The reaction scheme of Type IV compounds can be exemplified by 2'-0-[(2-chloropropyloxy)carbonyl]-paclitaxel which can be prepared as follows:

8.53 g (0.010 M) paclitaxel is dissolved in 200 ml anhydrous DE and to this mixture during the stirring is added dropwise at room temperature 3.05 g TEA (0.030 M) or 2.33 g (0.030 M) pyridine.

To this cold solution is added for few minutes dropwise 4.72 g (0.030 M) 2-chloro-propylchloroformate and the stirring continued 2 hours at 0° C.

After the reaction, the mixture is washed 3 times (each time with 150 ml) with water and the washed organic solution is dried on 10 g anhydrous $Na_2SO_4$ overnight.

The dry solution is filtered and concentrated to dryness on a Buchi Rotovapor at 40° C. and high vacuum.

The dry residue is then purified by a preparative HPLC on C-18 reversed phase with mobile phase 45/55 acetonitrile/water and recrystallized with 50/50 acetone/hexane.

7.85 g of white crystals (yield 80%) are obtained.

EXAMPLE 6

Variant B

The reaction scheme of Type IV compounds can also be exemplified by 2'-0-[2-chlorophenoxy(carbonyl]-paclitaxel which can be prepared as follows:

3.856 g (0.030 M) O-chlorophenol is dissolved in 250 ml anhydrous DE and the solution is cooled to 0° C.

Under N2 atmosphere at 0° C. and stirring, the solution is treated with 3.05 g (0.030 M) TEA and 3.33 g (0.012 M) solid triphosgene.

The stirring of the mixture at 0° C. is continued 1 hour to obtain freshly prepared 2-chloro-phenyl-chloroformate.

8.53 g (0.010 M) paclitaxel is dissolved in 120 ml anhydrous DE and stirred and cooled in an ice bath to 0° C.

Keeping the temperature around 0° C., the freshly prepared and cold solution of chloroformate is added to the paclitaxel solution, with stirring at 0° C. continued for 3 hours or more.

The cooling bath is removed and stirring of the mixture continued another 40 hours at room temperature.

A new portion of 2-chlorophenyl-chloroformate (0.012 M) prepared as above is added and stirring at room temperature is continued 3 days.

The reaction mixture (625–650 ml) is washed 3 times (each time with 500 ml) with water and the washed organic layer dried over 40 g anhydrous $Na_2SO_4$ overnight.

After filtration, the solution is concentrated on a Buchi Rotovapor at 40° C. and high vacuum to dryness.

The obtained crude product (11.5 g) is purified by preparative HPLC on a C-18 reversed phase column, using mobile phase 45/55 acetonitrile/water.

All fractions are checked by HPLC and those which contain only 2'-0-[2-chlorophenoxy(carbonyl]-paclitaxel are combined, concentrated, and sedimented material filtered on a Buchner funnel.

After drying the solid material is recrystallized from 50/50 acetone/hexane to obtain 4.93 g of white crystals (yield 50%).

EXAMPLE 7

The reaction scheme of Type IV compounds can further be exemplified by 2'-0-[2,4,6-tribromophenyloxy(carbonyl]-paclitaxel which can be prepared as follows:

8.53 g (0.101 M) paclitaxel is dissolved in 200 ml anhydrous DE and then cooled to 0° C. The solution is treated with 4.67 g (0.020 M) 2,4,6-tribromophenyl chloroformate dissolved in 50 ml of the same solvent.

The temperature is allowed to equilibrate and stirring of the reaction mixture is continued overnight.

The next day, the reaction mixture (250 ml) is washed 3 times (each time with 200 ml) with water and the organic solvent layer is dried with 10 g anhydrous $Na_2SO_4$ overnight.

The dry solution is filtered and concentrated on a Buchi Rotovapor at 40° C. and high vacuum to dryness.

The dry residue is purified by preparative HPLC using a column with C-18 reversed phase and 45/55 acetonitrile/water as mobile phase.

All fractions are checked by HPLC and those which contain 2'-0-[2,4,6-tribromophenyloxy(carbonyl]-paclitaxel are combined.

After concentration and sedimentation, the crude product is filtered, dried and recrystallized from 50/50 acetone/hexane to obtain 6.82 g of white solid material (yield 65%).

Synthesis of the Compounds of Type V

Halogenated analogues of Paclitaxel of the general structure of Type V of this invention can be prepared by the following synthetic routes:

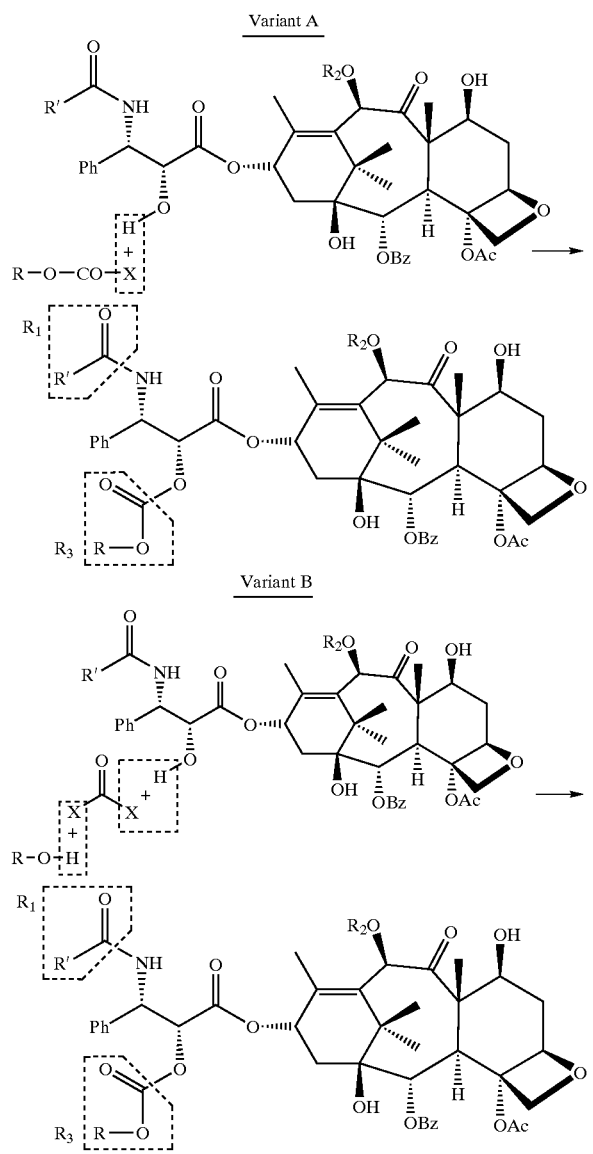

wherein
$R_1$ is a group selected from Table 1 (40 groups, 1–40);
$R_2$ is H or Ac;
$R_3$ is a group selected from Table 2 (55 groups, 41–95);

EXAMPLE 8

The reaction scheme in the production of Type V compounds is exemplified by N-(2"-bromo-3"-methyl)-butanoyl-2'-(2-bromo-ethoxy-carbonyl)-N-detygloyl-cephalomannine which can be prepared as follows:

8.93 g (0.010 M) N-(2"-bromo-3"-methyl)-butanoyl-N-detygloyl-cephalomannine is dissolved in 200 ml anhydrous DE and to this solution at room temperature is added dropwise 3.05 g TEA (0.030 M). The mixture is stirred and cooled to 0° C. in an ice bath.

To this cold solution is added dropwise for few minutes 5.63 g (0.030 M) 2-bromoethylchloro-formate and reaction mixture continued to be stirred for 3 hours at 0° C.

When the reaction is finished, the mixture is washed 3 times (each time with 150 ml) with water and the washed organic solution layer dried with 10 g anhydrous $Na_2SO_4$ overnight.

The dry organic solution is filtered from desiccant and the clear solution concentrated to dryness on a Buchi Rotovapor at 40° C. and high vacuum.

The obtained 10.4–11 dry material (residue) is purified by a preparative HPLC on a C-18 reversed phase column using mobile phase 45/55 acetonitrile/water.

The combined fractions which contains N-(2"-bromo-3"-methyl)-butanoyl-2'-(2-bromo-ethoxy-carbonyl)-N-detygloyl-cephalomannine are concentrated and sedimented product is recrystallized from 50/50 acetone/hexane.

7.3 g of white crystalline product (yield 65%) are obtained.

Synthesis of the Compounds of Type IX

Halogenated analogues of the general structure of Type IX of this invention can be prepared by the following synthetic routes:

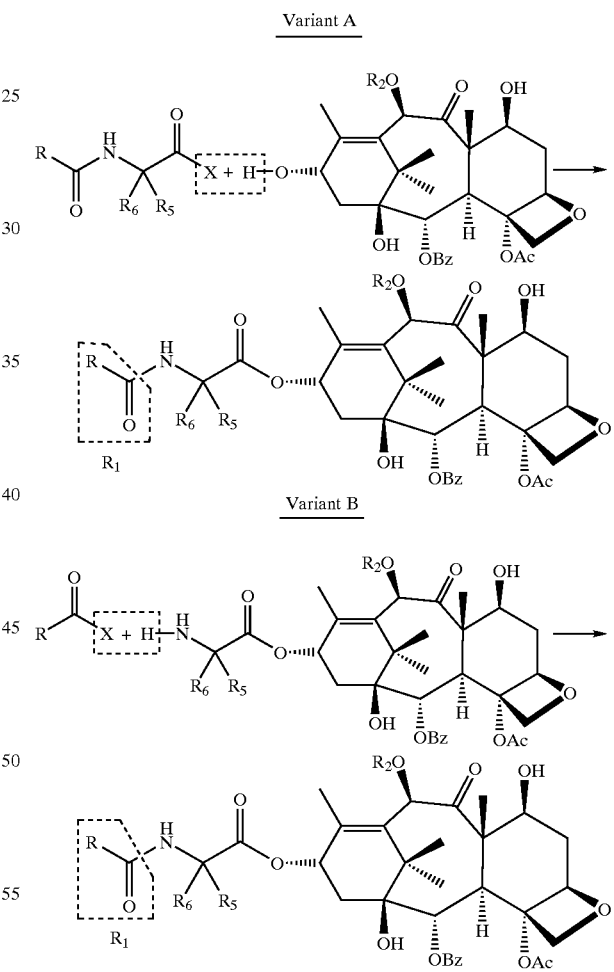

where
$R_1$ is a halogenated or dihalogenated acyl group (see Table 1, groups 1–40),
where $R_2$ is Ac or H and where $R_5$ is H or Me or Ac or Ph or Bz or $G_1$ or $G_2$ or $G_3$ or $G_4$ or $G_5$ or $G_6$ or $G_7$ or $G_8$ or $G_9$ $G_{10}$ or $G_{12}$ or $G_{13}$ (see Table 3).
$R_6$ is H;
in the case when $R_5$ is $G_{10}$, the group $R_6$ is H or Me;

Synthesis of Compounds of Type X

Halogenated analogs of the general structure of TypeX of this invention can be prepared by the following synthetic route:

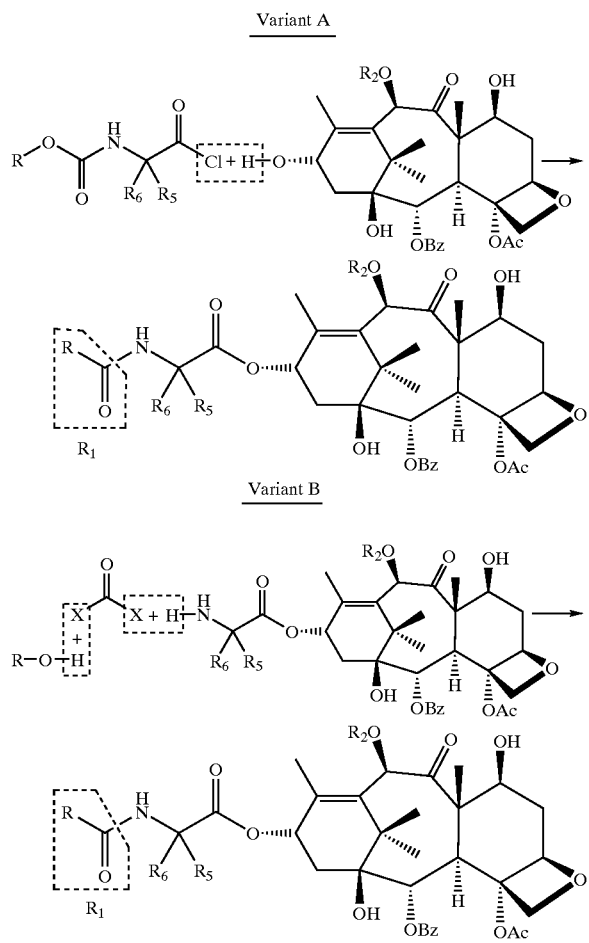

wherein $R_1$ is a halogenated formate (see Table 2, groups 41–95), where $R_2$ is Ac or H, and $R_5$ is H or Me or Ac or Ph or Bz or $G_1$ or $G_2$ or $G_3$ or $G_4$ or $G_5$ or $G_6$ or $G_7$ or $G_8$ or $G_9$ or $G_{10}$ or $G_{11}$ or $G_{12}$ or $G_{13}$ or $G_{14}$ (see Table 3.)

$R_6$ is H;

in the case when $R_5$ is $G_{10}$, the group $R_6$ is H or Me;

EXAMPLE 9

The reaction scheme of Type IX compounds is exemplified by 13-N-[(4-bromo-benzoyl)-alanyl]-Baccatin III which can be prepared as follows:

5.87 g (0.010 M) Baccatin III is dissolved in 200 ml anhydrous DE and to this solution at room temperature is added 2.05 g (0.030 M) TEA dissolved in 25 ml dry DE.

The mixture is stirred and cooled in an ice bath to 0° C. for about 1 hour.

During stirring at 0° C. 5.83 g (0.020 M) N-[(4-bromo-benzoyl)-alanyl chloride dissolved in 50 ml dry DE is added dropwise for about 30 minutes.

The stirring is continued at 0° C. overnight.

The next day, the mixture is neutralized and twice washed with 200 ml 0.5% $NaHCO_3$ to pH=6–7 (each time with 200 ml) with water.

The organic layer is dried over 20 g anhydrous $Na_2SO_4$ overnight, filtered and concentrated on a Buchi Rotovapor at 40° C. under high vacuum.

The dry residue is purified by preparative HPLC using a C-18 reversed phase column and mobile phase 45/55 acetonitrile/water. Combined fractions containing 13-N-[(4-bromo-benzoyl)-alanyl]-Baccatin III are concentrated to remove acetonitrile, sedimented material is filtered, dried and recrystallized from 50/50 acetone/hexane to obtain 5.85 g of white crystals (yield 70–72%).

EXAMPLE 10

The reaction scheme of Group VIII compounds is further exemplified by 13-N-[(4-chloro-ethoxy)-carbonyl]-alanyl-Baccatin III which can be prepared as follows:

5.87 g (0.010 M) Baccatin III is dissolved in 200 ml anhydrous DE and to this solution at room temperature is added 3.05 g TEA (0.030 M) dissolved in 25 ml dry DE.

The mixture is stirred and cooled in an ice bath to 0° C. (about 1 hour).

During the stirring at 0° C. for about 30 minutes 2.85 g (0.020 M) N-[(2-chloroethyloxy-carbonyl)-alanyl chloride dissolved in 50 ml dry DE is added dropwise for about 30 minutes.

The stirring is continued at 0° C. overnight.

The next day, the mixture is washed with 200 ml 0.5% $NaHCO_3$ to pH=6–6.5, then washed twice again, each time with 200 ml with water.

The organic layer is dried over 20 g $Na_2SO_4$ overnight, filtered and concentrated to dryness on a Buchi Rotovapor at 40° C. under high vacuum.

The solid residue is purified by preparative HPLC using a C-18 reversed phase column and mobile phase 45/55 acetonitrile/water.

Combined fractions containing 13-N-[(4-chloro-ethoxy)-carbonyl]-Baccatin III are concentrated to remove acetonitrile, sedimented material is filtered, dried and recrystallized from 50/50 acetone/hexane to obtain 5.5 g of white crystalline powder (yield 68–70%).

We claim:

1. Anti-neoplastic and/or anti-leukemic effective compound:

TYPE III

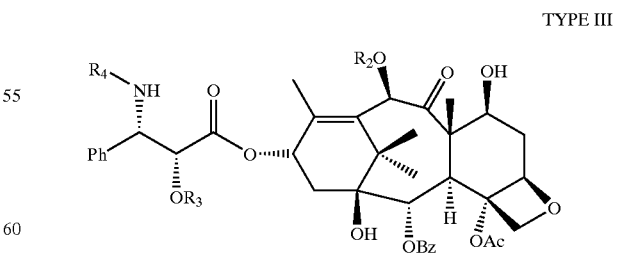

wherein $R_3$ is a group selected from the formulae of Table 1, groups I to 40, and $R_2$ is H or Ac; and $R_4$ is PhCO or $Me_3COCO$ or $CH_3CH=C(CH_3)CO$.

2. Anti-neoplastic and/or anti-leukemic effective compound:

TYPE IV

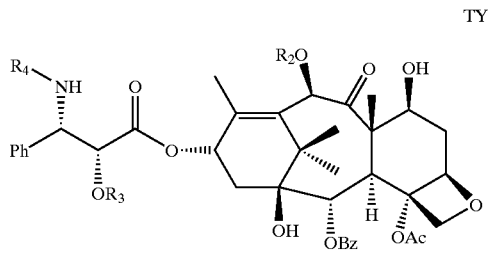

wherein $R_3$ is a group selected from the formulae of Table 2, groups 41 to 95;

$R_2$ is Ac or H; and $R_4$, is PhCO or $Me_3COCO$ or $CH_3CH=(CH_3)CO$.

3. Anti-neoplastic and/or anti-leukemic effective compound:

TYPE V

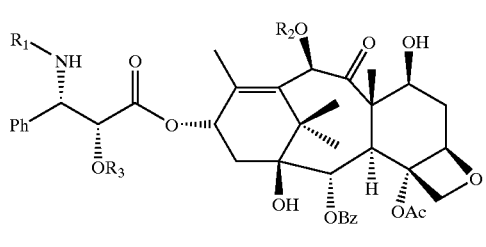

wherein $R_1$ is a group selected from the formulae of Table 1, groups 1 to 40;

$R_2$ is H or Ac;

$R_3$ is a group selected from the formulae of Table 2, groups 41 to 95.

4. Anti-neoplastic neoplastic and/or anti-leukemic effective compound:

TYPE VI

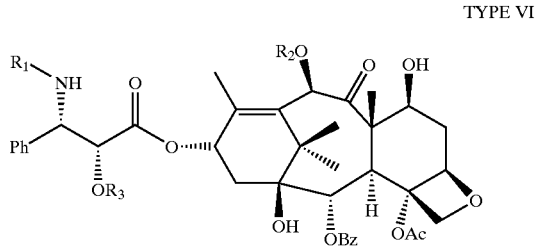

wherein $R_1$ is a group selected from the formulae of Table 2, groups 41 to 95;

$R_2$ is H or Ac;

$R_3$ is a group selected from the formulae of Table 1, groups 1 to 40.

5. Anti-neoplastic and/or anti-leukemic effective compound:

TYPE VII

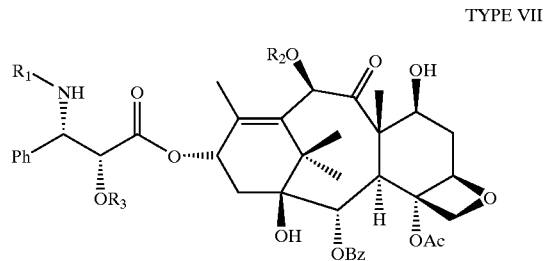

wherein $R_1$ is a group selected from the formulae of Table 1, groups 1 to 40;

$R_2$ is H or Ac;

$R_3$ is a group selected from the formulae of Table 1, groups 1 to 40.

6. Anti-neoplastic and/or anti-leukemic effective compound:

TYPE VIII

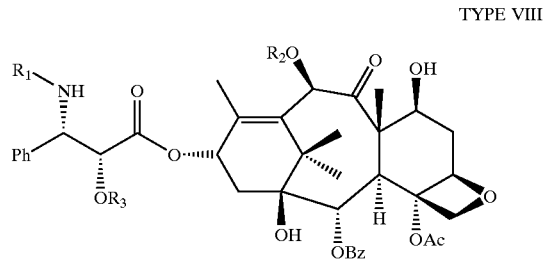

wherein $R_1$ is a group selected from the formulae of Table 2, groups 41 to 95;

$R_2$ is H or Ac;

$R_3$ is a group selected from the formulae of Table 2, groups 41 to 95.

7. Anti-neoplastic and/or anti-leukemic effective compound:

TYPE IX

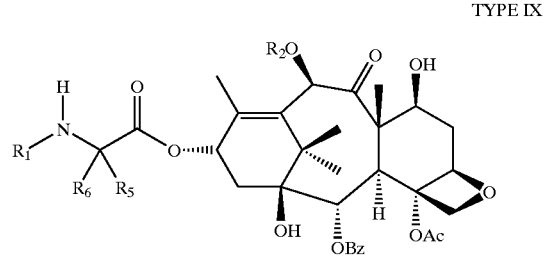

wherein $R_1$ is a group selected from the formulae of Table 1, groups 1 to 40;

$R_2$ is H or Ac;

$R_5$ is H or selected from the formulae of Table 3;

$R_6$ is H, and when $R_5$ is $G_{10}$ from Table 3, the group $R_6$ is H or Me.

8. Anti-neoplastic and/or anti-leukemic effective compound:

TYPE X

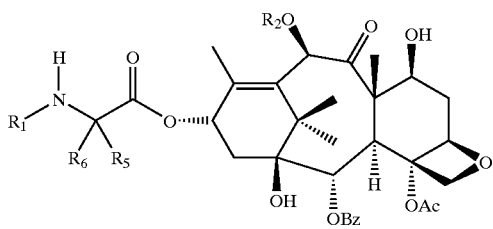

wherein $R_1$ is a group selected from the formulae of Table 2, groups 55 to 95;

$R_2$ is H or Ac;

$R_5$ is H or is selected from the formulae of Table 3;

$R_6$ is H and when $R_5$ is $G_{10}$ from Table 3, $R_6$ is H or Me.

9. A pharmaceutical formulation which comprises as an active ingredient a compound of claim 1 or a pharmaceutical acceptable salt thereof.

10. A pharmaceutical formulation which comprises as an active ingredient a compound of claim 2 or a pharmaceutical acceptable salt thereof.

11. A pharmaceutical formulation which comprises as an active ingredient a compound of claim 3 or a pharmaceutical acceptable salt thereof.

12. A pharmaceutical formulation which comprises as an active ingredient a compound of claim 4 or a pharmaceutical acceptable salt thereof.

13. A pharmaceutical formulation which comprises as an active ingredient a compound of claim 5 or a pharmaceutical acceptable salt thereof.

14. A pharmaceutical formulation which comprises as an active ingredient a compound of claim 6 or a pharmaceutical acceptable salt thereof.

15. A pharmaceutical formulation which comprises as an active ingredient a compound of claim 7 or a pharmaceutical acceptable salt thereof.

16. A pharmaceutical formulation which comprises as an active ingredient a compound of claim 8 or a pharmaceutical acceptable salt thereof.

17. A method for treating humans in need thereof comprising administering to said humans an anti-cancer or anti-leukemic effective amount of the compound of claim 1.

18. A method for treating humans in need thereof comprising administering to said humans an anti-cancer or anti-leukemic effective amount of the compound of claim 2.

19. A method for treating humans in need thereof comprising administering to said humans an anti-cancer or anti-leukemic effective amount of the compound of claim 3.

20. A method for treating humans in need thereof comprising administering to said humans an anti-cancer or anti-leukemic effective amount of the compound of claim 4.

21. A method for treating humans in need thereof comprising administering to said humans an anti-cancer or anti-leukemic effective amount of the compound of claim 5.

22. A method for treating humans in need thereof comprising administering to said humans an anti-cancer or anti-leukemic effective amount of the compound of claim 6.

23. A method for treating humans in need thereof comprising administering to said humans an anti-cancer or anti-leukemic effective amount of the compound of claim 7.

24. A method for treating humans in need thereof comprising administering to said humans an anti-cancer or anti-leukemic effective amount of the compound of claim 8.

25. A method for the production of a compound of claim 1 comprising reacting paclitaxel, cephalomannine or Taxotere® with halogenated or dihalogenated acyl halogenides selected from the formulae of Table 1, groups 1–40.

26. The method of claim 25 wherein the reaction is conducted in the presence of aminobases under temperatures effective to produce any amount of said compound.

27. A method for the production of a compound of claim 2 comprising,
    (a) reacting paclitaxel, cephalomannine or Taxotere® with halogenated alkyl or aryl formate selected from the formulae of (Table 2, groups 41 to 95, or
    (b) reacting paclitaxel, cephalomannine or Taxotere® with the product of the reaction between halogenated phenols selected from the formulae of Table 2, groups 41 to 95, and triphosgene.

28. The method of claim 27 wherein the reaction of part (b) is carried out with a non-separated and non-purified product obtained from said halogenated phenols and triphosgene under an inert atmosphere at temperatures effective to make any amount of said compound.

29. A method for the production of a compound of claim 3 comprising
    (a) reacting compounds of type 1

TYPE I

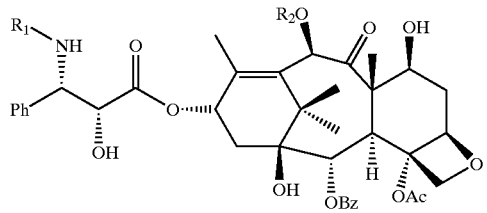

with halogenated alkyl or aryl formate selected from the formulae of Table 2, groups 41 to 95, or
    (b) reacting compounds of said type 1 with products obtained between halogenated phenols selected from the formulae of Table 2, groups 41 to 95, and triphosgene, at temperatures effective to make any amount of said compound.

30. A method for the production of a compound of claim 4 comprising reacting compounds of type II

TYPE II

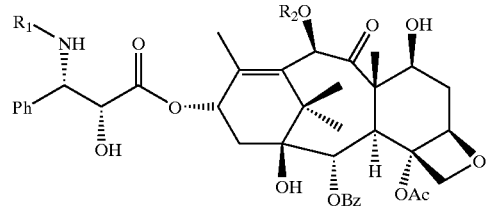

with halogenated or dihalogenated acyl halogenides selected from the formulae of Table 1, groups 1 to 40, in the presence of aminobases at temperatures effective to make any amount of said compounds.

31. A method for the production of a compound of claim 5 comprising reacting a compound of type 1

TYPE I

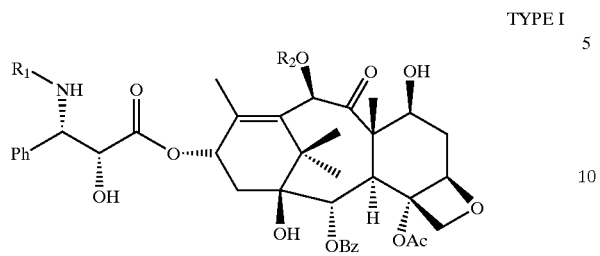

with halogenated or dihalogenated acyl halogenides selected from the formulae of Table 1, groups 1 to 40, in the presence of aminobases at temperature effective to make any amount of said compound.

32. A method for the production of a compound of claim 6 comprising (a) reacting compounds of type II

TYPE II

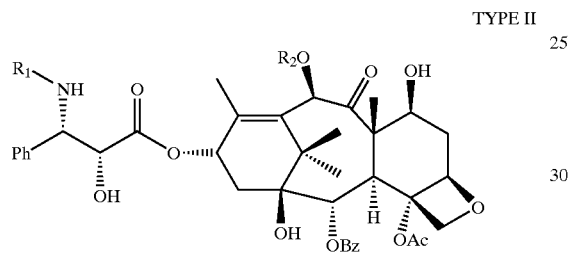

with halogenated alkyl or aryl formate selected from the formulae of Table 2, groups 41 to 95, or (b) reacting compounds of said type II with the products of the reaction between halogenated phenols selected from the formulae of Table 2, groups 41 to 95.

33. The method of claim 32 part (b) wherein the reaction is carried out under an inert atmosphere and at temperatures effective to make any amount of said compound.

34. A method for the production of a compound of claim 7 comprising (a) reacting N-substituted acyl halogenides selected from the formulae of Table 1, groups 1 to 40, α-amino acids when the group RCH(NH$_2$)COOH where R is selected from the formulae of Table 3, with

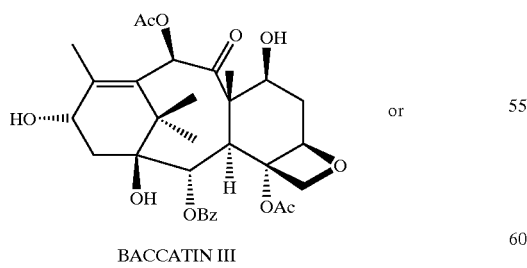

BACCATIN III or

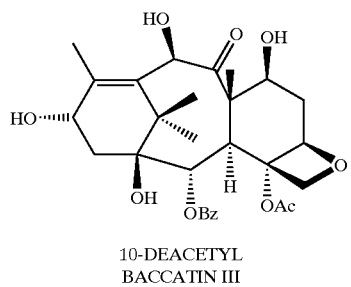

10-DEACETYL BACCATIN III in the presence of aminobases at a temperature effective to make any amount of said compound; or (b) reacting halogenated or dihalogenated acyl halogenides selected from the formulae of Table 1, groups 1–40, with esterified said α-amino acids selected from the formulae of Table 3, or with baccatin III or 10-deacetyl-baccatin III.

35. A method for the production of a compound of claim 8 comprising (a) reacting N-substituted halogenides selected from the formulae of Table 2, groups 41 to 95, with α-amino acids, (when the group RCH(NH$_2$)COOH, where R is selected from the formulae of Table 3), with,

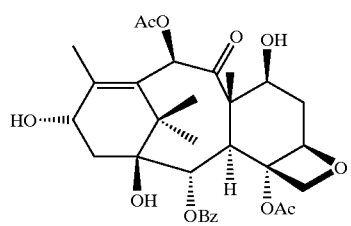

BACCATIN III

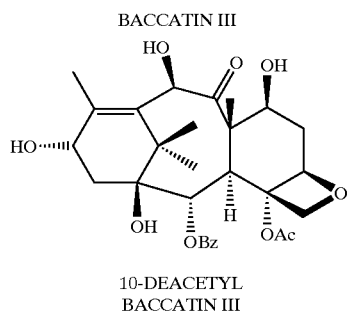

10-DEACETYL BACCATIN III in the presence of aminobases at temperatures effective to make any amount of said compound, or (b) reacting halogenated phenols selected from the formulae of Table 2, groups 41–95, and esterified said α-amino acids selected from the formulae of Table 3, with baccatin III or 10-deacetyl-baccatin III.

* * * * *